United States Patent

Hara et al.

[11] Patent Number: 5,275,624
[45] Date of Patent: Jan. 4, 1994

[54] DEVICE FOR INHIBITING AFTERCATARACT

[75] Inventors: Tsutomu Hara; Takako Hara, both of Utsunomiya; Yoshiharu Yamada, Nagoya; Yuriko Mizumoto, Nagoya; Hidenobu Nagai, Nagoya, all of Japan

[73] Assignee: Menicon Co., Ltd., Nagoya, Japan

[21] Appl. No.: 862,945

[22] Filed: Apr. 3, 1992

[30] Foreign Application Priority Data

Apr. 4, 1991 [JP] Japan ............................. 2-71894
Nov. 6, 1991 [JP] Japan ............................. 2-289940
Jan. 22, 1992 [JP] Japan ............................. 3-1826

[51] Int. Cl.$^5$ ............................................. A61F 2/16
[52] U.S. Cl. ............................................. 623/6; 623/4
[58] Field of Search ................ 623/4, 5, 6; 606/107; 604/294; 424/427

[56] References Cited

U.S. PATENT DOCUMENTS

| 4,764,169 | 8/1988 | Grendahl | 623/6 |
| 4,764,169 | 8/1988 | Grendahl | 623/6 |
| 4,781,717 | 11/1988 | Grendahl | 623/6 |
| 4,863,463 | 9/1989 | Tjan | 623/6 |
| 4,946,469 | 8/1990 | Sarfarazi | 623/6 |
| 5,026,396 | 6/1991 | Darin | 623/6 |

FOREIGN PATENT DOCUMENTS

| 2530457 | 1/1984 | France . |
| WO89/00032 | 1/1989 | World Int. Prop. O. . |
| WO89/07426 | 8/1989 | World Int. Prop. O. . |

Primary Examiner—Randall L. Green
Assistant Examiner—D. Willse
Attorney, Agent, or Firm—Nikaido, Marmelstein, Murray & Oram

[57] ABSTRACT

A device for inhibiting aftercataracts being made of a material having a resilient property and having substantially circular shape so as to internally contact an equator of a lenticular capsule. The device includes an aperture at a central portion thereof.

2 Claims, 12 Drawing Sheets

DEVICE FOR INHIBITING AFTERCATARACT

BACKGROUND OF THE INVENTION

The present invention relates to a device for inhibiting aftercataract (hereinafter referred to as an inhibiting device) and more particularly to an inhibiting device for keeping a shape of a lenticular capsule substantially circular after a crystalline lens is removed and for preventing an invasion of epithelial cells into a posterior lenticular capsule, and further to an inhibiting device wherein an intraocular lens can be retained in good condition by forming a groove in an inner periphery thereof.

As an operation method of crystalline lens, the method, wherein an anterior lenticular capsule is provided with an opening and a crystalline lens is removed through the opening, has hitherto been employed. A refraction of an eye is corrected by inserting an intraocular lens into the lenticular capsule instead of the removed crystalline lens, wearing a contact lens on a cornea, or wearing a pair of spectacles.

Figure 18:
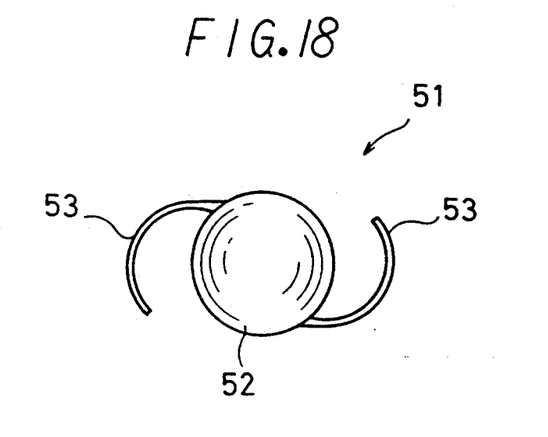
FIG. 18 is a plan view showing an example of a conventional intraocular lens.

When the intraocular lens is used, an intraocular lens such as lens 51 as shown in FIG. 18 has hitherto been used. The intraocular lens is composed of a lens 52 and two support members 53 having a wire like shape. The support member 53, wherein one end is fixed to the lens 52 and another end (outer side) is bended in such a manner as to extend along an equator of the lenticular capsule and contact with the equator, keeps the equator of the lenticular capsule circular. However, it is difficult for the above mentioned support member 53 to keep the equator of the lenticular capsule circular due to the shape thereof, and there is a danger that the support member adds an uneven force by partially contacting with the equator. Therefore, after inserting the intraocular lens into the lenticular capsule, the intraocular lens in the lenticular capsule becomes unstable after a long interval. Then, deviation or falling down of the intraocular lens sometimes happens.

Figure 19:
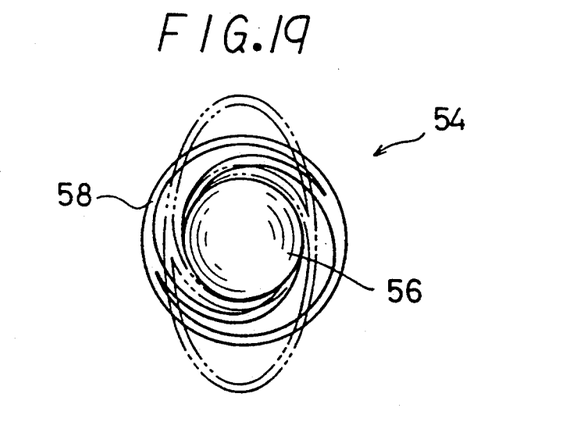
FIG. 19 is a plan view showing another example of a conventional intraocular lens.
Figure 20:
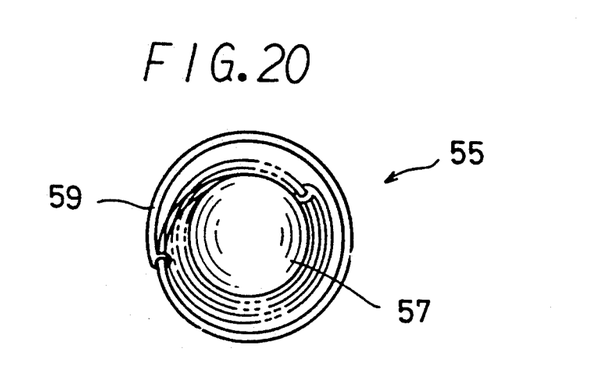
FIG. 20 is a plan view showing another example of a conventional intraocular lens.

The intraocular lenses 54, 55 shown in FIGS. 19 to 20 are proposed (with reference to Japanese Unexamined Patent Publication No. 285258/1989 and Japanese Unexamined Patent Publication No. 503525/1990). Each of the above lenses is composed of a lens portion 56, 57 and a support member 58, 59 which encloses the outer periphery of the lens portion having a circular loop like shape. The equator of the lenticular capsule can be kept to be circular in more preferable state compared with the intraocular lens of FIG. 18. It is difficult to insert the circular support member into the lenticular capsule through the incised opening as the original shape thereof. Therefore, the intraocular lens is inserted into the lenticular capsule by deflecting the support member to have an oval shape (referring to FIG. 19) or shrinking the support member in such a manner that circular shape thereof is kept (referring to FIG. 20).

The lenticular capsule after crystalline lens is removed sometimes happens to become opaque by proliferation, degeneration, or metaplasia of epithelial cells residual in the equator of the lenticular capsule if the capsule is left as it is. This phenomenon is generally called an aftercataract. A secondary operation typically needs to be performed to remove the aftercataract. As mentioned hereinbefore, when the intraocular lens is inserted into the lenticular capsule and the intraocular lens is fixed therein after the crystalline lens has been removed, there is such an intraocular lens as to inhibit the aftercataract to a certain extent by keeping the shape of the lenticular capsule and encircling the residual epithelial cell in the equator by virtue of the shape of the support member of the intraocular lens. However, the support member is not coming into contact with the whole part of the equator. Therefore, an aftercataract is not completely inhibited.

Further, when the lenticular capsule is left as it is for a long time without inserting the intraocular lens, the refraction of an eye should be corrected in such a manner that the contact lens is worn or a pair of spectacles is worn. In this case, an aftercataract is often produced in the lenticular capsule wherein the crystalline lens is removed. When the lenticular capsule is removed, such a complication that the vitreous body located in the back side of the eye goes forward is apt to come out. Accordingly, the lenticular capsule is not removed even if the intraocular lens is not inserted therein.

The object of the present invention is to resolve the problems mentioned hereinbefore and provide a device wherein an aftercataract is inhibited from forming and the circular shape of the equator can be kept stably.

SUMMARY OF THE INVENTION

A device for inhibiting aftercataracts of the present invention comprises a ring formed of a material having a resilient property, and having a substantially circular shape with an aperture at a central portion thereof, wherein said ring is used to contact an inner periphery of an equator of a lenticular capsule.

It is preferable that the inhibiting device has at least two protrusion portions which are formed in an outer periphery of the ring and intended to contact the inner periphery of the equator of the lenticular capsule.

Further, it is preferable that the device is provided with a groove for engaging with a support member of an intraocular lens in order to retain the intraocular lens. In this case, it is preferable that the groove is formed in the inner periphery of the device.

Further, it is preferable that the device comprises a front wall portion and a back wall portion, with the back wall portion adjacent to said groove, with the front wall portion and the back wall portion extending in the radial direction in such a manner that the back wall portion extends toward the center of the aperture by a first distance, and the front wall portion extends toward the center of the aperture by a second distance which is less than said first distance.

The meaning of "having substantially a circular shape" mentioned in the claims is a concept including not only a complete round but also a polygonal shape so that the outer periphery of the device can be internally touched to the whole of the equator of the lenticular capsule. The meaning of "a front wall portion" is one of side walls located in the front side of the device when the device is implanted in the eye and the meaning of "a back wall portion" is the other side wall located in the back side of the device when the device is implanted in the eye.

The device of the present invention is easily deformed in accordance with the desired shape by pinching the device slightly by means of a forceps and the like. Therefore, a special technique for inserting is not required and the device is easily inserted into the lenticular capsule through even a small incised opening by means of Continuous Circular Capsulorhexis (CCC) method. After inserting the device into the lenticular capsule, the device returns to the circular shape, which is an original shape, by means of the resilient property of the device. Accordingly, the outer periphery of a ring of the inhibiting device is in contact with the equator in the lenticular capsule, encircling the epithelial cells which are residual within the portion between the equator and the outer periphery of the inhibiting device, so that proliferation of the residual epithelial cells can be inhibited in good condition. On the other hand, the equator of the lenticular capsule can be kept almost circular by virtue of the shape of the device. Therefore, the lenticular capsule is given to a tension so that the lenticular capsule is effectively inhibited from shrinking. Thus, the aftercataract can be inhibited by the effect of the device.

Further, the shape of the incised opening is kept and the intraocular lens can be easily inserted into the lenticular capsule by the tension thereof. In this case, when the device having a groove in the inner periphery thereof is used, the support member of the intraocular lens inserted into the lenticular capsule is engaged with the groove formed in the inner periphery of the device and fixed thereto. As a result, the intraocular lens is prevented from deviating from the intended location.

DETAILED DESCRIPTION

Figure 1:
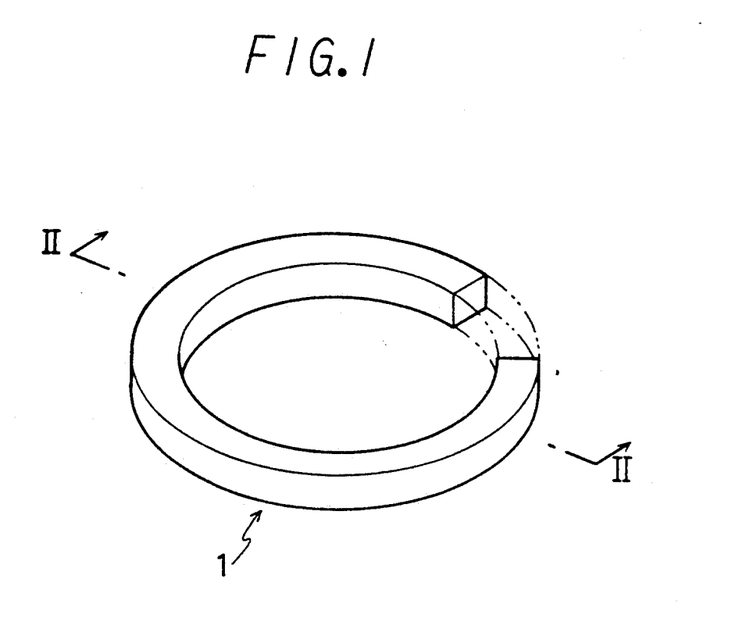
FIG. 1 of the invention is a partially cutaway perspective view showing an embodiment of an inhibiting device of the present invention.
Figure 2:
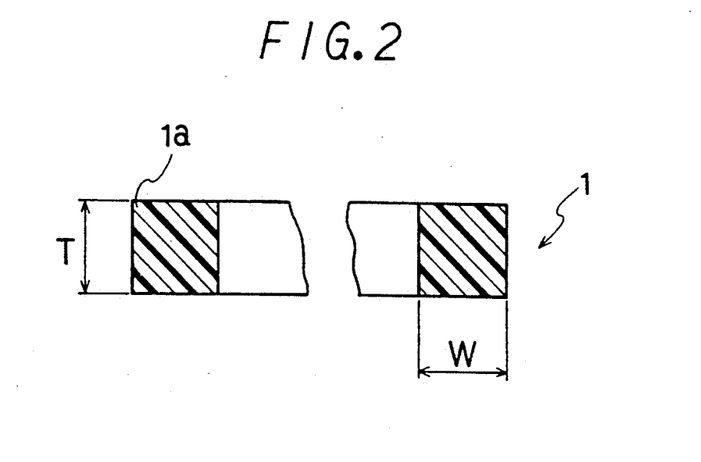
FIG. 2 is a partially schematic sectional view taken along lines II—II in FIG. 1.
Figure 3:
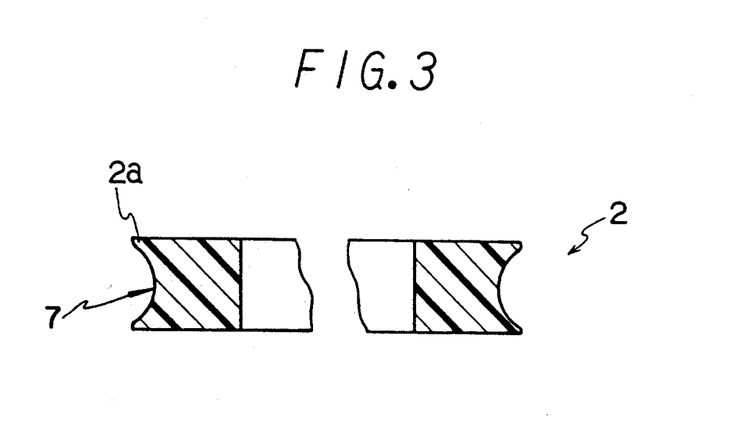
FIG. 3 is a partially schematic sectional view showing another embodiment of the inhibiting device of the present invention.

In FIG. 1, numeral 1 denotes an inhibiting device comprising a ring having a circular shape with an aperture of a central portion thereof. An outer diameter is about 10 mm, an inner diameter is about 8 mm and each of width (W in FIG. 2) and thickness (T in FIG. 2) is respectively about 1 mm. Those sizes are values which are determined by a normal size of a lenticular capsule. Accordingly, the outer diameter and the thickness are not limited to the above size. For instance, with respect to the outer diameter, a range of 8 to 12 mm is general and with respect to the thickness, a range of 0.4 to 2.0 mm is general. A shape in section of a ring portion of the inhibiting device is substantially square wherein a length of each side is about 1 mm as shown in FIG. 2. In the present invention, any shape in section of the outer periphery of the device 1 can be employed, wherein residual epithelial cells can be encircled within a portion between the equator and the outer periphery of the device in good state. The shape in section is not limited to a square shape; such a shape as shown in FIG. 3 can be employed.

In the device 1 having a square shape in section as shown in FIG. 2, corner portions 1a wherein protrusions are formed in the whole of the outer periphery are coming into substantially linear contact with the lenticular capsule. Accordingly, the residual epithelial cells can be sealed in the equator of the lenticular capsule in good state and the lenticular capsule can be prevented from producing an aftercataract caused by a proliferation, degeneration, or metaplasia of the residual epithelial cells. Then, the aftercataract which becomes a problem after removing the crystalline lens can be effectively inhibited. The inhibiting device 2 shown in FIG. 3 has also the corner portion 2a wherein the protrusions are formed in the whole of the outer periphery. Therefore, the protrusions of the corner portion 2a cause the same effect as corner portions 1a. The inhibiting device 2 has a recess 7 which is grooved centripetally between the corner portions 2a. Therefore, when the device 2 is inserted into the eye as mentioned hereinafter, the device can be easily bended by engaging a forceps and the like with the recess.

Figure 4:
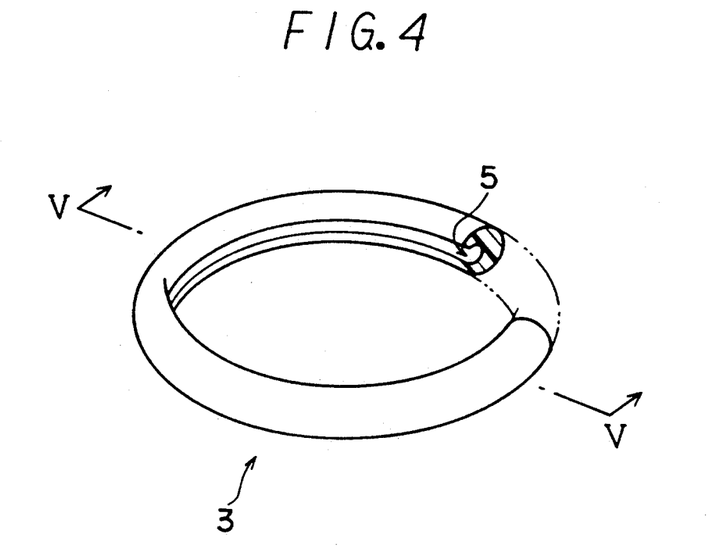
FIG. 4 is a partially cutaway sectional view showing another embodiment of the device of the present invention.
Figure 5:
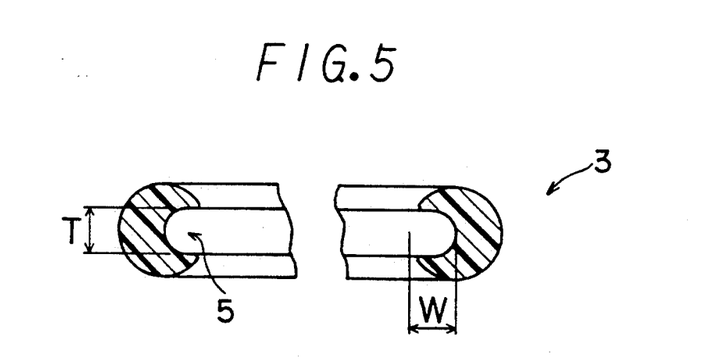
FIG. 5 is a partially schematic sectional view taken along lines V—V in FIG. 4.
Figure 6:
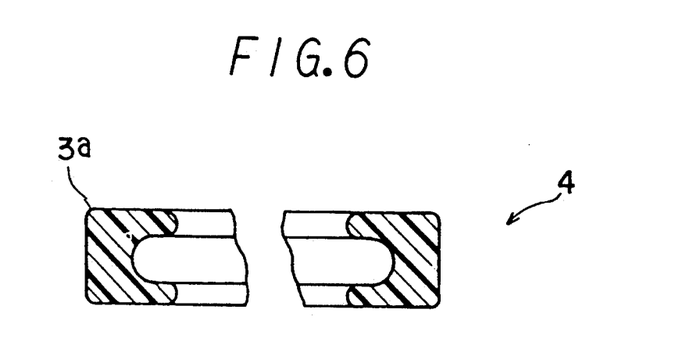
FIG. 6 is a partially schematic sectional view showing another embodiment of the device of the present invention.
Figure 7:
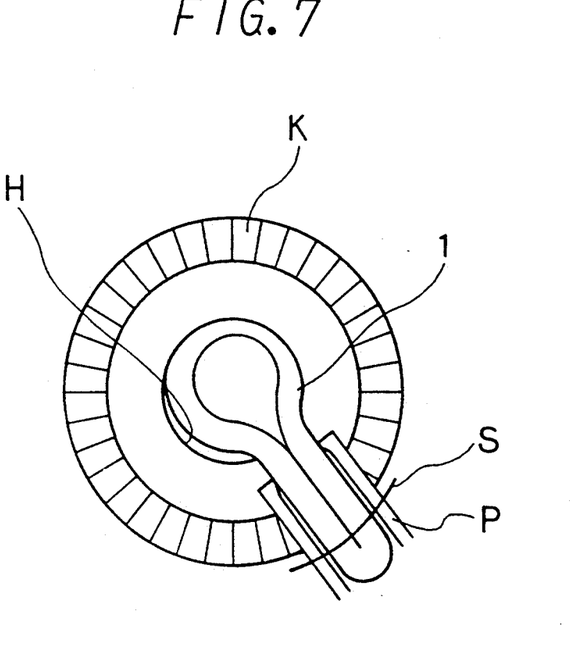
FIG. 7 is an explaining view showing a use of the device of FIG. 1.

On the other hand, in FIGS. 4 to 6, the devices 3, 4, wherein a groove 5 for retaining a support member of an intraocular lens is formed in the whole of the inner periphery, are shown. The width W of the groove 5 shown in FIG. 5 is about 0.5 mm and the depth T of the groove 5 is about 0.5 mm. The size of the groove 5 is also determined by the size of the support member of the intraocular lens. Accordingly, in the device of the present invention, the size of the groove is not limited to the above value. Further, in the present invention, the groove is not necessarily limited in such a manner that the groove is formed in the whole of the inner periphery of the device, even in a manner wherein the groove is partially or intermittently formed can be employed in accordance with the shape of the support member of the intraocular lens which can engage with the inhibiting device. However, the groove 5 which is formed in the whole of the inner periphery is preferably employed in order to cope with all kinds of intraocular lenses and all kinds of methods for inserting the intraocular lenses.

According to the conventional intraocular lens 54, 55 (referring to FIGS. 19 to 20), even if the intraocular lens is made to be such a means as to be easily inserted into the lenticular capsule, when the intraocular lens 54 shown in FIG. 19 is inserted into the lenticular capsule, the support member of the intraocular lens is permitted to become an oval like shape (shown with two-dot chain line in FIG. 19) so that a major axis of the oval is still longer than an inner diameter (about 10 mm in a normal case) of the lenticular capsule. Accordingly, the intraocular lens 54 is difficult to be inserted into the lenticular capsule. On the other hand, with respect to the intraocular lens 55 shown in FIG. 20, such a particular technique of inserting the intraocular lens into the lenticular capsule has been required that the intraocular lens is shrunk (i.e. diameter of the intraocular lens is shortened) by winding the support member 59 along the periphery of the lens portion 57 and the above state of the intraocular lens is kept. Further, the incised opening for inserting the intraocular lens into the lenticular capsule tends to be small, for fear that the eye be damaged. Therefore, it is still more difficult to be inserted.

The device of the present invention can resolve the above problems. A stably fixed state is ensured by engaging the support member of the intraocular lens with the groove 5 formed in the inner periphery of the inhibiting device 3, 4 as mentioned hereinbefore.

In the inhibiting device 3 shown in FIGS. 4 to 5, the shape in section of the ring is a substantially circular shape wherein the diameter is about 1 mm. The shape in section is not limited to the circular shape in the present invention. The inhibiting device wherein the shape in section is square as shown in FIG. 6 can be employed.

If the equator is closely contacted with the inhibiting device so that there is not any space to proliferate the residual epithelial cells in the equator of the lenticular capsule, the aftercataract can be inhibited in spite of the circular shape in section of the inhibiting device.

When the shape in section of the ring is circular, the contacting surface wherein the outer periphery of the device 3 comes into contact with the inner wall of the lenticular capsule is wide. Therefore, stress concentration can be effectively avoided. In the device 4 wherein the shape in section is square as shown in FIG. 6, the corner portions 3a located in the outer periphery come into substantially linear contact with the lenticular capsule. Therefore, the residual epithelial cells can be encircled in the equator of the lenticular capsule as mentioned hereinbefore, and the effect, wherein an aftercataract causing a postoperative problem is inhibited, is superior.

As a material of the devices 1 to 4, and the devices 11 and 12 of the embodiment mentioned hereinafter, a material which has a resilient property in order to insert the inhibiting device into the lenticular capsule and stably fix therein, is selected. In the preferred embodiment, silicone rubber is employed as the material. If the material is suitable for ophthalmic treatment (for instance, if the material has a suitability in vivo, a stability of the shape and the like), the material is not limited in the present invention, for instance polymers having water absorption property comprising hydroxyethylmethacrylate, N-vinylpyrrolidone, vinyl alcohol and the like, a biopolymer comprising collagen and the like, and an elastomer silicone rubber, acrylic rubber and the like and a mixture or copolymer of these materials can be employed.

Further, such a synthetic resin having an inferior clarity as to be normally used as a medical material such as polyethylene, polypropylene vinyl chloride, polyvinylidenefluoride and the like can be employed, and even a hard synthetic resin such as polymethylmethacrylate can be employed as the material of the device if the resilient property is given by suitably selecting the shape or thickness.

The inhibiting devices 1 to 4 of the above-mentioned embodiment and the devices 11 and 12 of the embodiment mentioned hereinafter, which are constructed by a single material in consideration of an ease of manufacturing in such a manner as to be integrated, can be easily manufactured by means of molding.

Next, it will be explained with reference to FIGS. 7 to 13 how to use the device constructed according to the invention. In FIGS. 7 to 13, character K denotes a mydriatic iris, character H denotes an incised opening located in the anterior lenticular capsule, character S denotes an incised opening located in a sclera, character P denotes a forceps. Firstly, a crystalline lens is removed through the incised opening H and the incised opening S and viscomaterial is fully injected into an anterior chamber and the lenticular capsule of the eye. Then, the device is pinched by the forceps so that the shape thereof becomes almost oval. Next, the deformed inhibiting device is inserted into the lenticular capsule through the incised openings S and H (referring to FIGS. 7 and 9). In order to insert the inhibiting device 1 into the lenticular capsule, a tool other than the forceps such as a commercial injector for a soft IOL (intraocular lens) can be employed. When the device is inserted into the lenticular capsule, the device 1 restores the original circular shape by means of the resilient property. Accordingly, the device comes into contact with the whole of the equator of the lenticular capsule (referring to FIG. 8 and 10). Thereby, the residual epithelial cells in the equator are sealed therein. Further, the lenticular capsule is given a tension to maintain the substantially circular shape. Therefore, a shrinkage of the lenticular capsule is effectively inhibited and an aftercataract can be inhibited from being formed.

Figure 8:
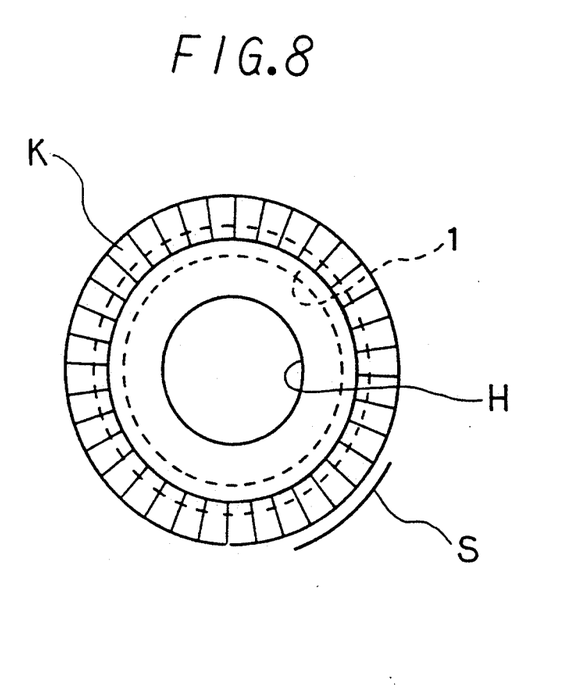
FIG. 8 is an explaining view showing a use of the device of FIG. 1.
Figure 9:
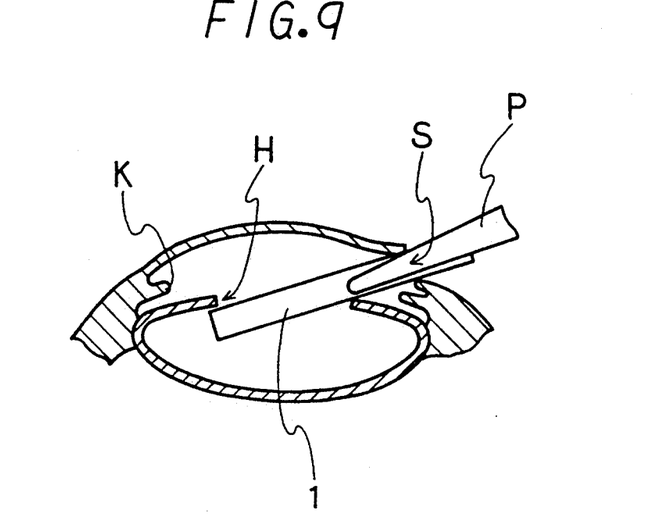
FIG. 9 is an explaining view showing a use of the device of FIG. 1.
Figure 10:
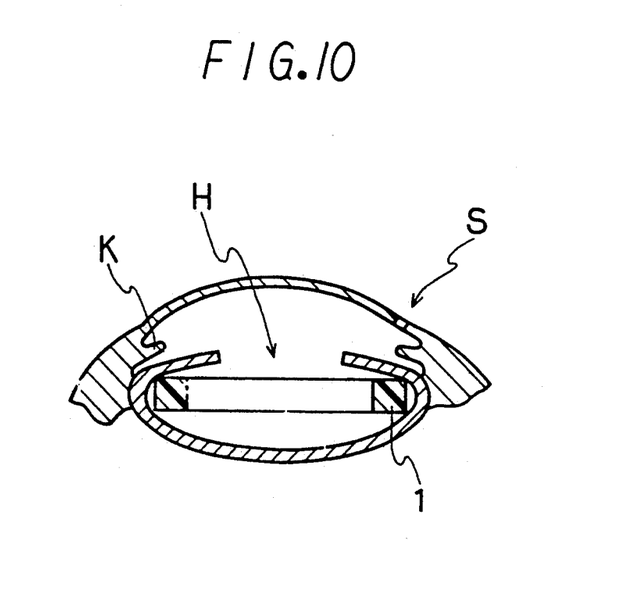
FIG. 10 is an explaining view showing a use of the device of FIG. 1.
Figure 11:
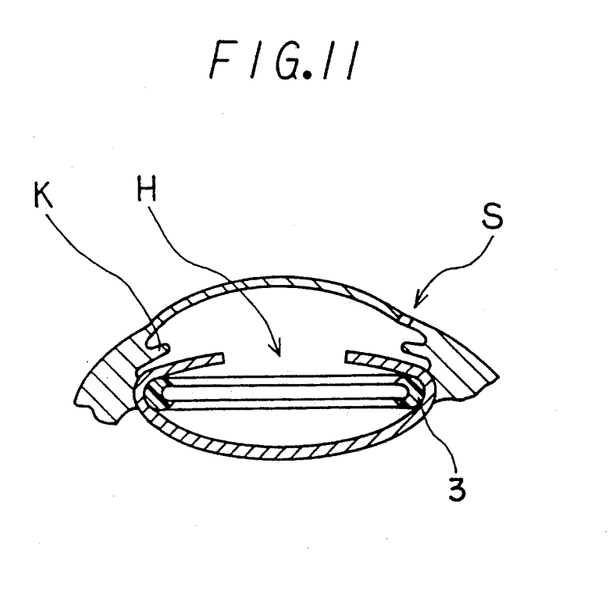
FIG. 11 is an explaining view showing a use of the device of FIG. 4.
Figure 12:
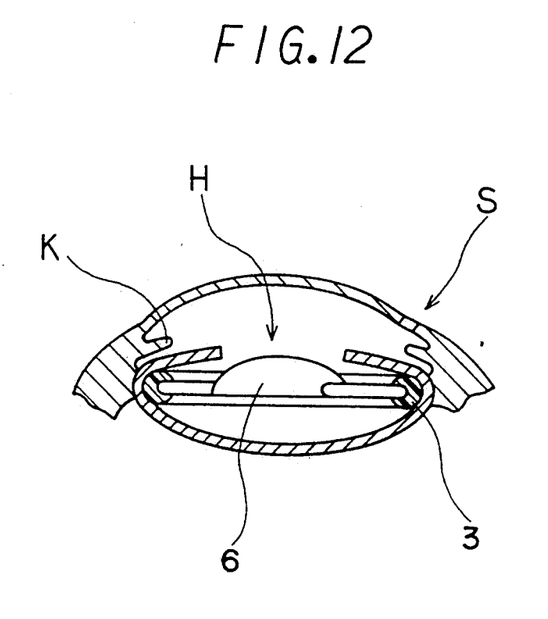
FIG. 12 is an explaining view showing a use of the device of FIG. 4.
Figure 13:
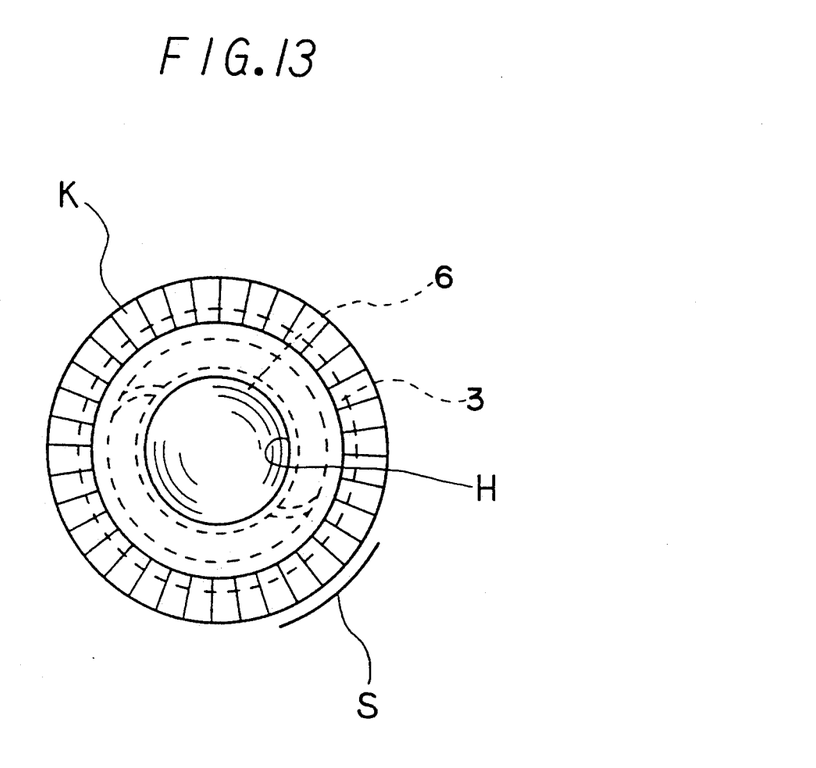
FIG. 13 is an explaining view showing a use of the device of FIG. 4.

Further, the equator is kept circular and the incised openings S and H maintain the shape (referring to FIGS. 8 and 10). Therefore, the intraocular lens, which is generally used, can be easily inserted into the lenticular capsule through the incised openings S and H. In this case, if the inhibiting device 3, 4 having a groove is employed, (referring to FIG. 11), it does not happen that the intraocular lens deviates or falls down since the support member of the intraocular lens is engaged with the groove of the device so that intraocular lens is stably fixed (referring to FIGS. 12 and 13).

Figure 14:
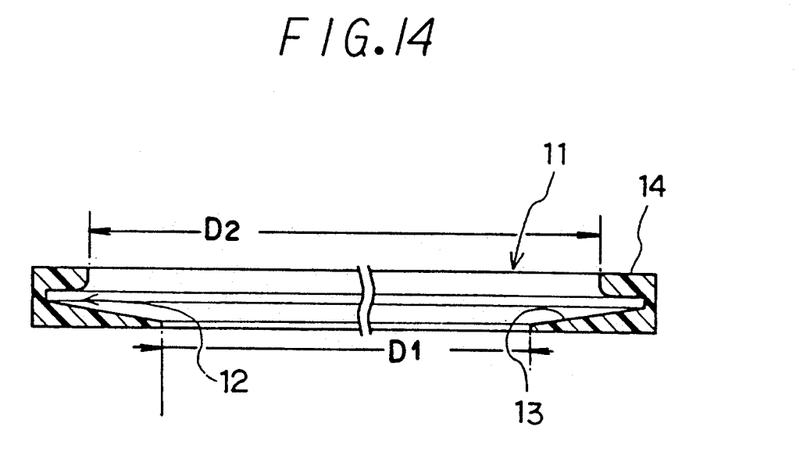
FIG. 14 is a partially schematic sectional view showing another embodiment of the device of the present invention.

In FIG. 14, the other embodiment of the inhibiting device which has a groove in the inner periphery is shown.

The device 11 is an example of variation of the device 4 in FIG. 6. The device 11 comprises a ring member having a "U" shape in cross section, a groove 12, and wall members 13 and 14. Groove 12 is formed with front wall 14 and back wall 13 and is formed in the whole of the inner periphery of the inhibiting device 11. Back wall 13 extends in a radial direction toward a center of the aperture creating a first inner diameter D1, and the front wall 14 extends toward the center creating a second inner diameter D2 which is greater than the first diameter D1. Therefore, the front wall extends toward the center of the aperture by a distance which is less than the distance by which the back wall extends toward the center of the aperture. Back wall 13 is tapered in such a manner that a thickness in the direction of the back wall 13 increases in a radially outward direction.

The back wall can be constructed in such a manner that the back wall has a circular shape which is almost concentric to the outline (circular shape) of the device when the device is viewed from the upper side (i.e. the back wall is circular shaped). Such a construction can be also employed that the back wall portion, wherein the support member of the intraocular lens is inserted, extends toward a center of the ring. In short, any shape can be employed if the optical portion of the intraocular lens to be inserted into the device can be secured, the support member of the intraocular lens can be easily engaged with the groove of the device and easily deformed when the device is inserted into the lenticular capsule. For instance, the inner diameter of the back wall is preferably 5 to 7.5 mm in accordance with the object of the present invention.

In the present invention, the device is not limited to the device wherein the shape in section is square (FIG. 14). The inhibiting device 3 of FIGS. 4 to 5 having a circular shape in section, wherein the back wall is protruded, can be employed.

Figure 15:
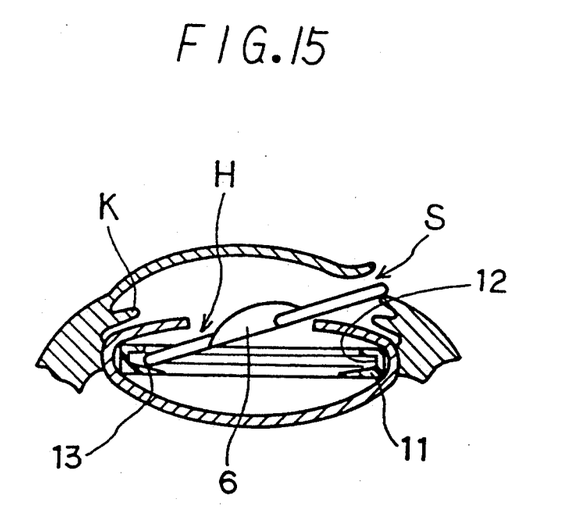
FIG. 15 is an explaining view showing a use of the device of FIG. 14.

It will be explained with reference to FIG. 15 as follows how to use the inhibiting device 11. Firstly, the device 11 is inserted into the lenticular capsule. The inserting method is the same as mentioned hereinbefore. Secondly, the intraocular lens 4 is inserted into the lenticular capsule. At this time, the support member of the intraocular lens is contacted with a slanting surface of the back wall 13. Then the support member moves along the slanting surface due to the resilient restoring force thereof and extends to the groove 12 so that the support member is completely contained in the groove 12. In other words, the back wall 13 which extends toward a center of the ring acts to guide the support member of the intraocular lens 6 so that the intraocular lens can be easily and surely inserted and securely held. Since the back wall 13 is centripetally protruded, an ophthalmologist who performs an operation can not only confirm the back wall 13 of the device which is inserted into an eye and set but also insert and fix the intraocular lens easily and surely.

Figure 16:
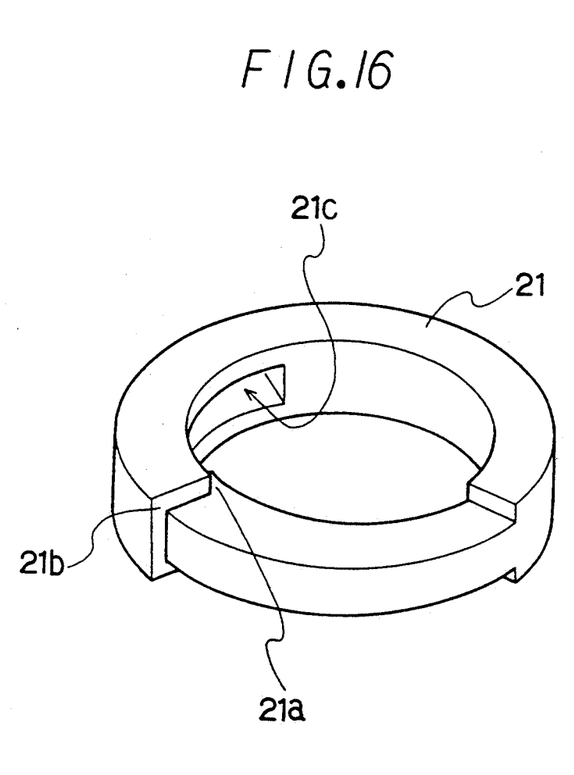
FIG. 16 is a perspective view showing another embodiment of the device of the present invention.
Figure 17:
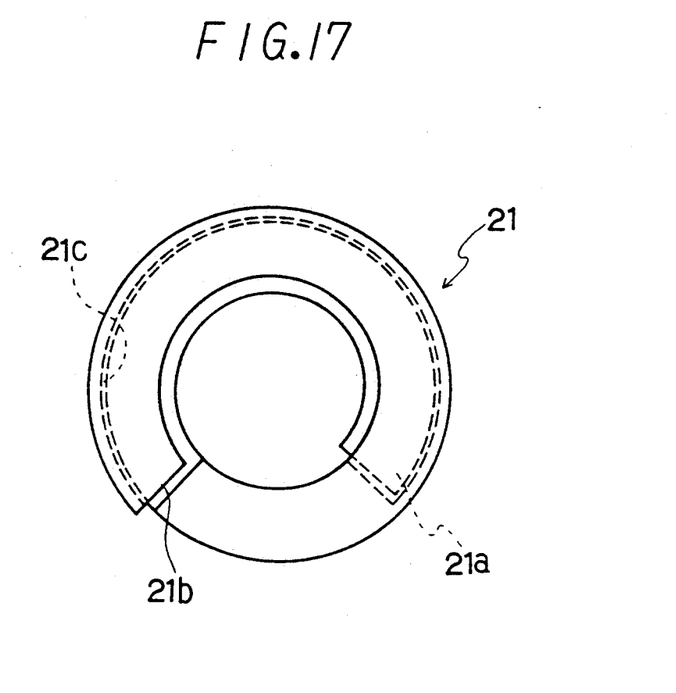
FIG. 17 is an explaining view showing a use of the device of FIG. 16.

In FIG. 16, another embodiment of the device is shown. This embodiment does not have the groove The device 21 is an example of a variation of the inhibiting device 1 shown in FIG. 1. The device has such a construction that one end 21a of the device is inserted into a channel 21c which is formed from the other end 21b.

Thus constructed device 21 can shorten the outer diameter thereof in such a manner that one end 21a is inserted into the channel 21c. Therefore, the device can be still more easily inserted into the eye. By inserting the device into the lenticular capsule, the device completely comes into contact with the equator of the lenticular capsule, the residual epithelial cells in the equator of the capsular bag can be encircled in the equator and aftercataract caused by proliferation of cells can be effectively inhibited. Further, since the device can keep the shape of the lenticular capsule circular, shrinkage of the lenticular capsule is inhibited and aftercataract can be effectively inhibited.

On the other hand, since the device can keep the shape of the lenticular capsule circular, the shape of the incised opening is kept in good state. Therefore, when the intraocular lens is inserted after the crystalline lens is removed, the intraocular lens can be easily inserted and it does not happen that the intraocular lens damages the incised opening by adding unstable force. In this case, the intraocular lens can be firmly retained and inhibited from falling down and moving, then can be fixed in good state by using an inhibiting device having a groove.

Though several embodiments of the present invention are described above, it is to be understood that the present invention is not limited only to the above-mentioned, and various changes and modifications may be made in the invention without departing from the spirit and scope thereof.

We claim:

1. A device for inhibiting an aftercataract, comprising:

a ring formed of a material having a resilient property, and having a substantially circular shaped with an aperture at a central portion thereof, said ring including a groove formed in an inner periphery thereof, said groove structured to engage with a support member of an intraocular lens in order to retain the intraocular lens, wherein said ring is sized to contact an inner periphery of an lenticular capsule, said ring further comprising a front wall portion and a back wall portion adjacent to said groove, said back wall portion and said front wall portion extending in a radial direction in such a manner that said back wall portion extends toward a center of the aperture by a first distance, and wherein, in a non-flexed condition, the front wall portion extends toward the center of the aperture by a second distance which is less than the first distance, said back wall portion being tapered in such a manner that a thickness in the axial direction of the back wall portion increases in a radially outward direction.

2. A device for inhibiting an aftercataract of claim 5 which has at least two protrusion portions which are intended to contact said inner periphery of the equator of the lenticular capsule.

* * * * *

UNITED STATES PATENT AND TRADEMARK OFFICE
CERTIFICATE OF CORRECTION

PATENT NO. : 5,275,624
DATED : Jan. 4, 1994
INVENTOR(S) : Baudendistel

It is certified that error appears in the above-indentified patent and that said Letters Patent is hereby corrected as shown below:

On the title page, Item [30], third line, change "3-1826" to -- 4-1826 --.

Signed and Sealed this

Sixth Day of September, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,275,624
DATED : January 4, 1994
INVENTOR(S) : Tsutomu Hara et al

It is certified that error appears in the above-indentified patent and that said Letters Patent is hereby corrected as shown below:

On the title page, Item [30], third line, change "3-1826" to -- 4-1826 --.

This certificate supersedes Certificate of Correction issued September 6, 1994

Signed and Sealed this

Fourteenth Day of March, 1995

Attest:

BRUCE LEHMAN

Attesting Officer    Commissioner of Patents and Trademarks